United States Patent
Powell et al.

(10) Patent No.: US 10,112,041 B2
(45) Date of Patent: Oct. 30, 2018

(54) IMPLANTABLE CONNECTOR CLEANING SYSTEM

(71) Applicant: Cochlear Limited, Macquarie University, NSW (AU)

(72) Inventors: Anthony Powell, Macquarie University (AU); C. Roger Leigh, East Ryde (AU); James Dalton, Beecroft (AU)

(73) Assignee: Cochlear Limited, Macquarie University, NSW (AU)

( * ) Notice: Subject to any disclaimer, the term of this patent is extended or adjusted under 35 U.S.C. 154(b) by 669 days.

(21) Appl. No.: 13/921,920

(22) Filed: Jun. 19, 2013

(65) Prior Publication Data

US 2014/0379059 A1    Dec. 25, 2014

(51) Int. Cl.
*A61N 1/05* (2006.01)
*A61B 18/00* (2006.01)
*H01R 13/621* (2006.01)

(52) U.S. Cl.
CPC ...... *A61N 1/05* (2013.01); *A61B 2018/00178* (2013.01); *A61B 2562/227* (2013.01); *H01R 13/621* (2013.01); *H01R 2201/12* (2013.01)

(58) Field of Classification Search
None
See application file for complete search history.

(56) References Cited

U.S. PATENT DOCUMENTS

| | | | |
|---|---|---|---|
| 4,971,057 A | 11/1990 | Theres | |
| 7,534,127 B2* | 5/2009 | Parker | A61N 1/36032 439/425 |
| 7,844,329 B2 | 11/2010 | Chambers | |
| 9,065,197 B2* | 6/2015 | Powell | H01R 13/5219 |
| 2006/0076433 A1* | 4/2006 | Darling, III | A61L 2/22 239/302 |
| 2009/0155325 A1* | 6/2009 | Wenzel | A61F 13/8405 424/402 |

FOREIGN PATENT DOCUMENTS

WO    2004/097993    11/2004

* cited by examiner

*Primary Examiner* — Michael E Barr
*Assistant Examiner* — Jason Riggleman
(74) *Attorney, Agent, or Firm* — Pilloff & Passino LLP; Martin J. Cosenza (57) ABSTRACT

A system for cleaning mating parts of an implantable connector includes an implantable connector and a cleaning structure. The implantable connector includes first and second detachable mating parts configured: to be implantable in living tissue; to terminate at least a first segment of a cable; and to have with first and second interfacing surfaces, respectively. The clean structure includes: a cleaning structure configured to clean the first and second interfacing surfaces as the first and second mating parts are being engaged.

29 Claims, 9 Drawing Sheets

IMPLANTABLE CONNECTOR CLEANING SYSTEM

BACKGROUND

Field of the Invention

The present technology relates generally to detachable mating parts of an implantable connector that terminate at least one segment of a cable.

Related Art

In an implantable apparatus, a cable (e.g., including one or more electrical conductors) configured with at least one segment that terminates in an implantable connector which has corresponding detachable mating parts facilitates replacement of other parts of the apparatus, e.g., when such other parts fail, are consumed, or are in need of being updated. For example, an implantable connector on a device requiring an implanted battery facilitates replacement of the battery.

For some implantable connectors, it is important to exclude body fluids from the mating surfaces of the mating parts. Body fluids are ionic, which can cause current leakage between the conductors in the short term. In the long term, ionic body fluids may precipitate dendritic growth between the mating surfaces, which can contribute to device failure.

On the occasion of decoupling and re-coupling the detachable mating parts of such a connector in a surgical environment where body fluids present, e.g., in a context of replacing an expired battery, exposure of the mating surfaces of the mating parts to the bodily fluids is a risk. To reduce the risk, some surgeons physically manipulate the mating parts in an attempt to reduce the chances of exposure of the mating surfaces to the body fluids, e.g., by lifting and/or turning the mating parts away from the tissue at the implantation site (to the extent possible).

SUMMARY

In one aspect of the present technology, a system for cleaning mating parts of an implantable connector is provided. The system for cleaning mating parts of an implantable connector includes an implantable connector and a cleaning structure. The implantable connector includes first and second detachable mating parts configured: to be implantable in living tissue; to terminate at least a first segment of a cable; and to have with first and second interfacing surfaces, respectively. The clean structure includes: a cleaning structure configured to clean the first and second interfacing surfaces as the first and second mating parts are being engaged.

In another aspect of the present technology, a method for cleaning mating parts of an implantable connector is provided. Such a connector includes first and second detachable mating parts configured to be implantable in living tissue, to terminate at least a first segment of a cable, and to have first and second interfacing surfaces, respectively. Such a method includes: applying a layer of cleaning material to at least one of the first and second mating parts, the cleaning material being a foam material or a viscous material; and engaging the first and second mating parts so as to compress the layer of cleaning material between the first and second interfacing surfaces of the engaging first and second mating parts, thereby expelling a portion of the cleaning material from between the first and second mating parts.

In yet another aspect of the present technology, an implantable connector is provided. Such a connector includes first and second detachable mating parts, each being configured: to be implantable in living tissue: and to terminate at least a first segment of a cable, respectively. Each of the first and second mating parts includes first and second resilient cleaning structures having first and second interfacing surfaces, respectively, that are convex. Such first and second resilient cleaning structures are configured to progressively deform as the first and second mating parts become progressively more engaged with each other. And a degree of contact between the first and second interfacing portions progressively increases as the first and second mating parts become progressively more engaged, thereby progressively expelling material from between the first and second mating parts as the degree of contact becomes progressively greater.

In yet another aspect of the present technology, a system for cleaning a mating part of an implantable connector is provided. Such a system includes: a first detachable mating part and a protection structure. The first detachable mating part is configured to be implantable in living tissue, terminate a segment of a cable, have an interfacing surface; and engage with a corresponding second detachable, implantable mating part. The protection structure is configured to facilitate removal of contamination from the interfacing surface.

In yet another aspect of the present technology, a system for transporting a mating part of an implantable connector is provided. Such a system includes: a first detachable mating part and a transportation structure. The first mating part is configured to be implantable in living tissue, terminate a segment of a cable, and engage with a corresponding second detachable, implantable mating part. The transportation structure is configured for mounting the first mating part thereon.

BRIEF DESCRIPTION OF THE DRAWINGS

Embodiments of the present technology are described below with reference to the attached drawings, in which:

FIG. 1A is a three-quarter perspective view, FIG. 1C is an exploded three-quarter perspective view.

FIG. 8A is a three-quarter perspective view.

DETAILED DESCRIPTION

Figure 1A:
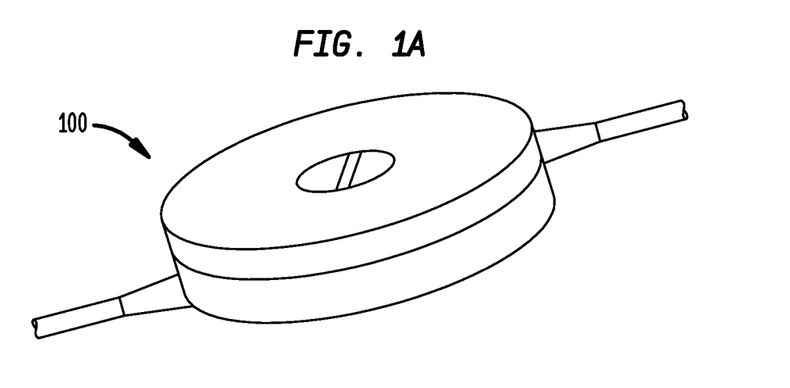
Figure 1B:
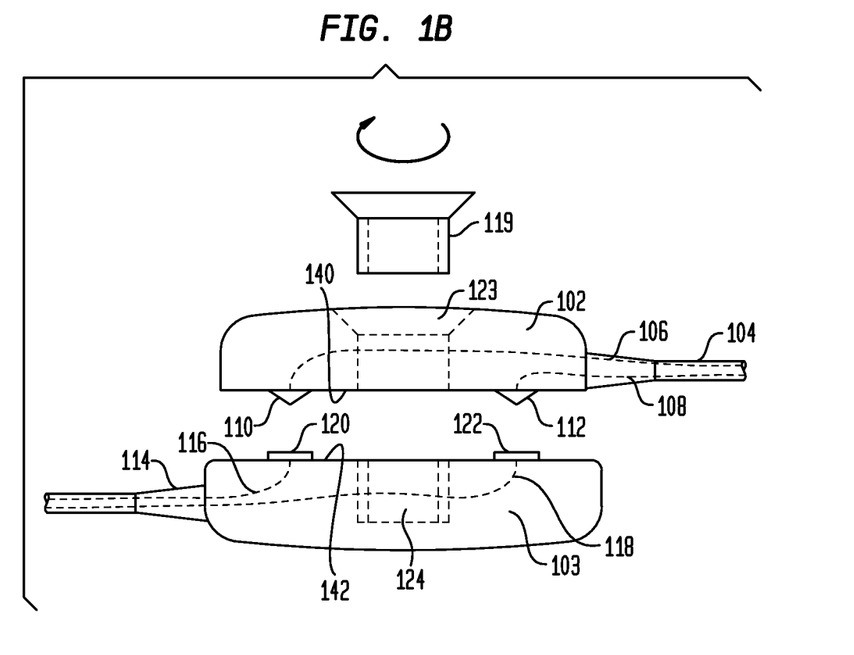
FIGS. 1B and 1D are cross sections (FIG. 1D being relatively simplified), of an implantable connector.
Figure 1C:
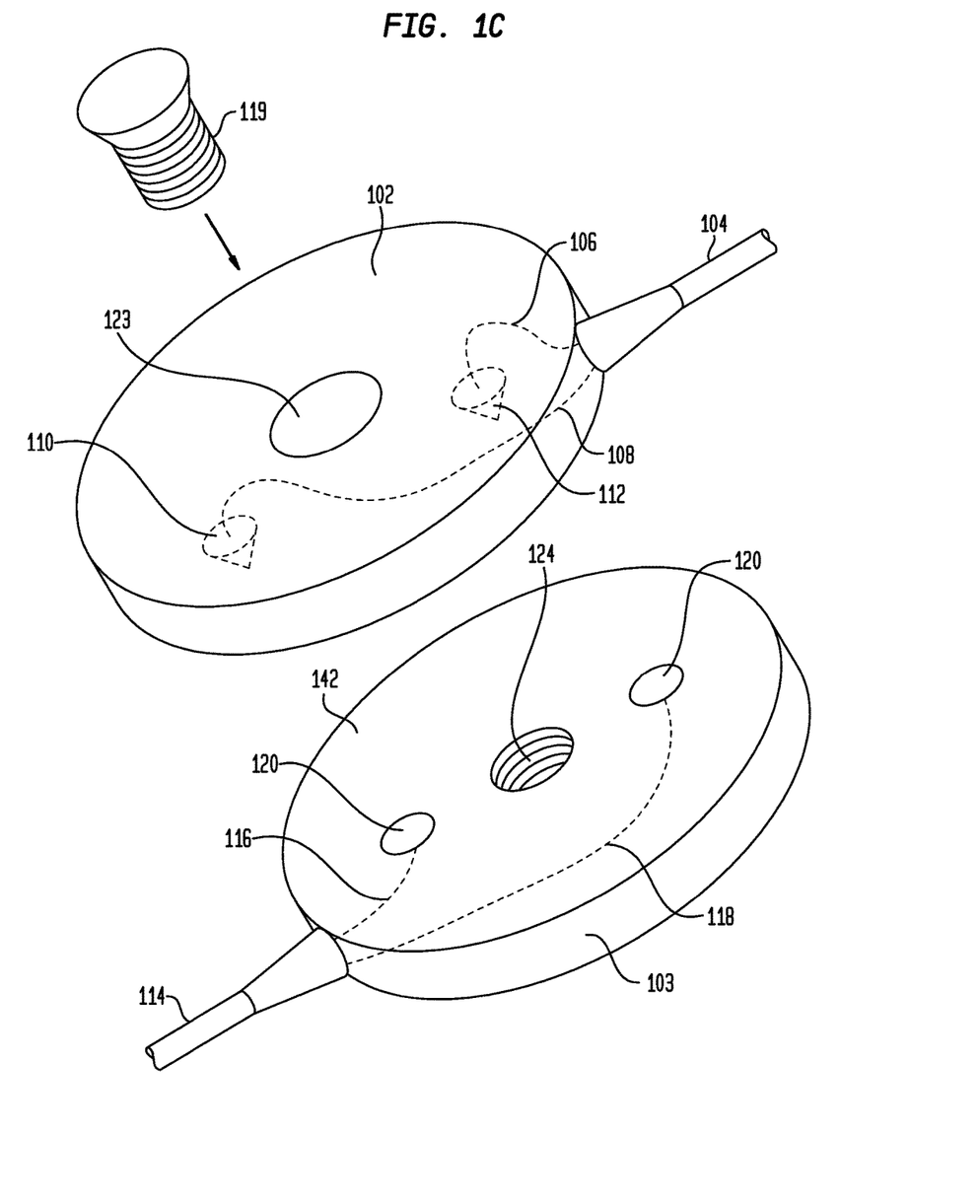

FIG. 1A is a three-quarter perspective view of an implantable connector 100. FIG. 1B is an exploded side view of connector 100. And FIG. 1C is an exploded three-quarter perspective view of implantable connector 100.

Implantable connector 100 is a button type of connector that includes: a first detachable mating part 102 and a second detachable mating part 103 corresponding thereto. Mating parts 102 and 103 terminate a first segment 104 and a second segment 114 of a cable. In FIGS. 1B-1C, the cable is illustrated as including first and second signal lines, the first signal line including segments 106 and 116, the second signal line including segments 108 and 118. Mating parts 102 and 103 have interfacing surfaces 140 and 142, respectively. Signal line segments 106 and 108 are connected to electrodes 110 and 112 located on interfacing surface 140, respectively, and signal line segments 116 and 118 are connected to electrodes 120 and 122 located on interfacing surface 142, respectively. It is noted that fewer and greater numbers of signal lines and corresponding electrodes are contemplated. On any given signal line, various signals are contemplated as being conducted, e.g., power, data, control, communication, etc., respectively. While electrodes 110 and 112 are illustrated as having triangular cross sections, and electrodes 120 and 122 are illustrated as having rectangular cross sections, other shapes are contemplated for the electrodes. While illustrated as being a button type, other types of connectors are contemplated for connector 100. The various components of connector 100 are formed of biocompatible materials, e.g., including one or more of Titanium, Silicone, Ceramic, Platinum, Platinum/Iridium, polyether ether ketone (PEEK), etc.

Connector 100 also includes, for example, a frictional engaging member 119, e.g., a screw, that can be inserted through a corresponding through-hole (e.g., unthreaded) 123 in mating part 102 and into a corresponding complementarily-shaped frictional engaging recess 124, e.g., a threaded hole, in mating part 103. When inserted through through-hole 123 into hole 124, screw 119 applies a force to mating part 102 that urges mating part 102 to abut mating part 103, i.e., urges mating part 102 to couple with mating part 103. More particularly, the force applied by screw 119 urges electrodes 110 and 112 to abut and thus to connect to electrodes 120 and 122, respectively. The force applied by screw 119 also resists a tendency of mating parts 102 and 103 to decouple. In addition, holes 123 and 124 are formed in alignment so that the insertion of screw 119 causes mating parts 102 and 103 to align, thereby facilitating good electrical connections between corresponding electrodes 110 and 120, and corresponding electrodes 112 and 122.

Figure 1D:
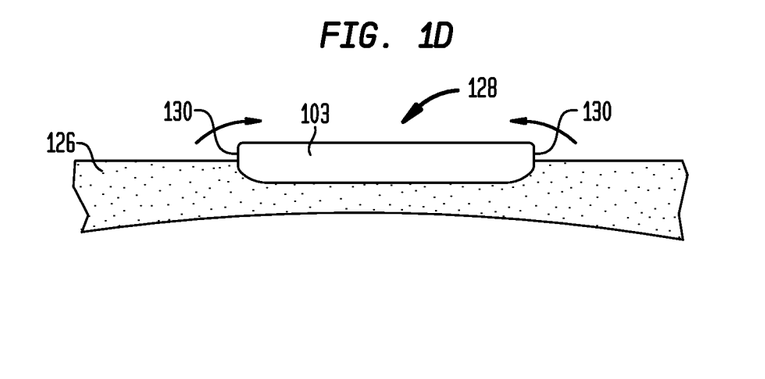

FIG. 1D illustrates one of mating parts 102 and 103, e.g., 103, implanted in bone 126, e.g., in the midst of a surgical procedure, e.g., a procedure to replace an instance of mating part 102 ("replacee mating part 102") by another instance of mating part 102 ("replacer mating part 102") while mating part 103 remains in its implanted position. When replacee mating part 102 is decoupled from mating part 103, a surface 128 of mating part 103 on which the electrodes are located is placed at risk of contamination by body fluids that wash over sidewalls 130 of mating part 103. Mating parts 102 and 103 also can begin in a decoupled state before they are initially coupled (e.g., such as when mating part 103 is implanted albeit before being initially coupled with mating part 102), during which time surface 128 of mating part 103 is similarly at risk of contamination by body fluids that wash/seep/migrate over sidewalls 130.

Figure 2A:
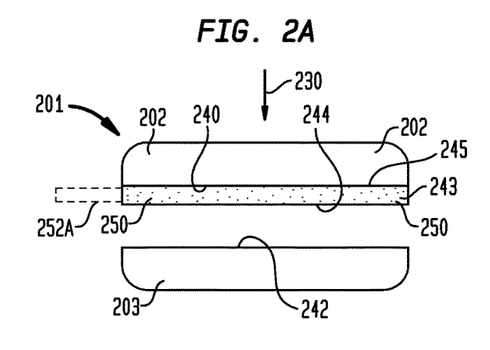
FIG. 2A is an exploded cross section of a system, in which some embodiments of the present technology may be implemented, for cleaning mating parts of an implantable connector.

FIG. 2A is an exploded cross section of a system 201, in which some embodiments of the present technology may be implemented, for cleaning mating parts of an implantable connector 200. Connector 200 is similar in many respects to connector 100 of FIGS. 1A-1C, as indicated by similar numbering, and in some respects has been illustrated in less detail for the sake of brevity.

System 201 includes implantable connector 200, e.g., a button type of connector. Connector 200 includes: a first detachable mating part 203 and a corresponding second detachable mating part 202, each of mating parts 202 and 203 being configured to be implantable in living tissue and terminate first and second segments (not illustrated) of a cable, respectively. Mating parts 202 and 203 have interfacing surfaces 240 and 242. Corresponding electrode pairs (not illustrated) are provided on interfacing surfaces 240 and 242. FIGS. 2A, 2B, 2D and 2F assume that mating part 203 is partially recessed in bone 126. The various components of connector 200 are formed of biocompatible materials, e.g., including one or more of Titanium, Silicone, Ceramic, Platinum, Platinum/Iridium, polyether ether ketone (PEEK), etc.

Connector 200 also includes, for example, a frictional engaging member (not illustrated), e.g., a screw, that can be inserted through a corresponding through-hole (not illustrated), e.g., an unthreaded through-hole, in mating part 202 and into a corresponding complementarily-shaped frictional engagement recess (not illustrated), e.g., a threaded hole, in mating part 203. When inserted through the through-hole into the hole, the screw applies a force to mating part 202 that urges mating part 202 to abut mating part 203, i.e., urges mating part 202 to couple with mating part 203. More particularly, the force applied by the screw urges corresponding electrode (not illustrated) in pairs thereof to abut and thus to connect electrically, respectively. The force applied by the screw also resists a tendency of mating parts 202 and 203 to decouple. In addition, the through-hole and hole formed in mating parts 202 and 203, respectively, are formed in alignment so that the insertion of screw causes mating parts 202 and 203 to align, thereby facilitating good electrical connections between corresponding electrodes 210 and 220, and corresponding electrodes 212 and 222.

In FIG. 2A, mating parts 202 and 203 are illustrated in a decoupled state. As noted, e.g., a decoupled state can arise in the context of a surgical procedure, e.g., a procedure to replace an instance of mating part 202 ("replacee mating part 202") by another instance of mating part 202 ("replacer mating part 202") while mating part 203 remains in its implanted position, e.g., implanted in bone, or mating parts 202 and 203 can begin in a decoupled state before they are initially coupled, etc. Assuming the replacement scenario for the purposes of discussion, when replacee mating part 202 is decoupled from mating part 203, interfacing surface 242 of mating part 203 on which electrodes 220 and 222 are located is placed at risk of contamination by body fluids that wash over the sidewalls.

To protect against such a risk, system 201 further includes: a cleaning structure 250 configured to clean interfacing surfaces 240 and 242 as mating parts 202 and 203 are being engaged, as denoted by arrow 230. Cleaning structure 250 can be, e.g., a dry wipe or a wet wipe. Wipe 250 can be removably attached to interfacing surface 240 of mating part 202 so as to seal interfacing surface 240 from the ambient environment.

Wipe 250 can include one or more woven or nonwoven fabrics. Amongst nonwoven fabrics, wipe 250 can be any of various types of nonwoven fabric, e.g., spunlaced (hydroentangled), carded, wetlaid, spunlaid, spunmelt, spunbonded, meltblown, spun-melt-spun (SMS), airlaid, needle-punched, etc. Wipe 250 can include, e.g., one or more of viscose fibers, polyester fibers, cotton fibers, polyactic acid (PLA) fibers, etc. If wipe 250 is a wet wipe, then it is contemplated that wipe 250 will be moistened with one or more appropriate cleaning liquids. If wipe 250 is a dry wipe, then it is contemplated that one or more appropriate cleaning liquids would be applied to wipe 250 at the time of preparing to engage mating parts 202 and 203. While mating parts 202 and 203 are being compressed together (e.g., by hand, by a tool, etc.), and before the screw is inserted so as to extend from second mating part 202 into mating part 203. Wipe 250 can be withdrawn from between interfacing surfaces 240 and 242.

Optionally, wipe 250, for example, can be further configured with a hole 260 through which passes the portion of the screw that extends from second mating part 202 into mating part 203. Optionally, wipe 250 can be further configured to facilitate being cleaved, at least in part, by the screw as wipe 250 is being withdrawn from between interfacing surfaces 240 and 242. Wipe 250 can include one or more optional tabs, e.g., 252A in FIG. 2A, that overhang one or more corresponding edges of interfacing surfaces 204 and 242. Each of tabs 252A and 252B is configured to be grasped and thereby used to transfer a withdrawal force to wipe 250 by which to withdraw at least a corresponding part of wipe 250 from between interfacing surfaces 240 and 242.

Optionally, wipe 250 can be further configured with one or more sets 262 of tear perforations corresponding to the one or more tabs 252A and 252B, each of sets 252A and 252B of tear perforations being located on a side of hole 260 substantially along a radius extending from the hole along at least one of the following directions: a direction substantially opposite to the corresponding tab; and a direction substantially perpendicular to the corresponding tab.

Figure 2B:
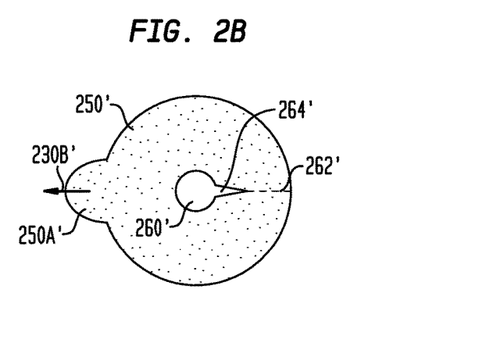
FIG. 2B is a top view of another wipe, according to another embodiment of the present technology.
Figure 2C:
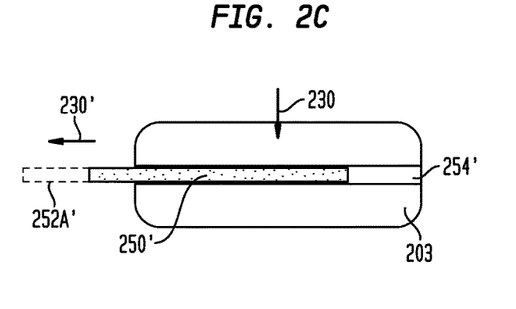
FIG. 2C is a cross section illustrating a later stage in the engagement of the mating parts relative to the stage illustrated by FIG. 2A.

FIG. 2B is a top view of a wipe 250', according to another embodiment of the present technology. FIG. 2C is a cross section illustrates a later stage in the engagement of mating parts 202 and 203 relative to the stage illustrated by FIG. 2A, later in the process of clamping of wipe 250' by mating parts 202' and 203'. Wipe 250' is similar in many respects to wipe 250 of FIG. 2A, as indicated by similar numbering.

In FIG. 2C, a force substantially parallel to a withdrawing direction 230' has been applied to tab 252', causing wipe 250' to be moved in direction 230', thereby cleaning surfaces 240 and 242. The removal of wipe 250' leaves a gap 254' between interfacing surfaces 240 and 242, with the length of gap 254' increasing as wipe 250 becomes progressively further withdrawn from mating parts 202 and 203, and with the height of gap 254' decreasing as mating parts 202 and 203 become progressively further engaged. FIG. 2F is a cross section showing connector 200 after mating parts 202 and 203 are fully engaged.

In FIG. 2B, an optional set 262' of tear perforations is located along a radius extending from hole 260' along a direction substantially opposite to the direction of tab 250A'. In FIG. 2C, as a consequence of a portion of wipe 250 being dragged past the screw (not illustrated), wipe 250' has begun to be cleaved, as indicated by split 264'.

Figure 2D:
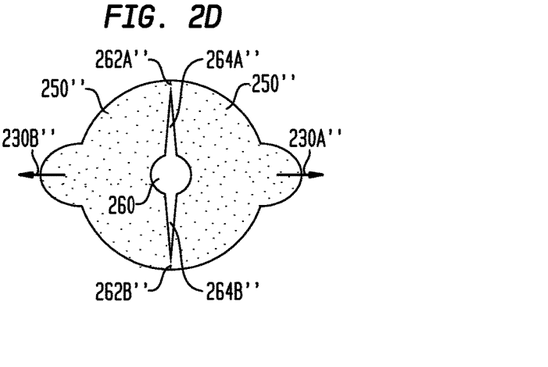
FIG. 2D is a top view of yet another wipe, according to another embodiment of the present technology.
Figure 2E:
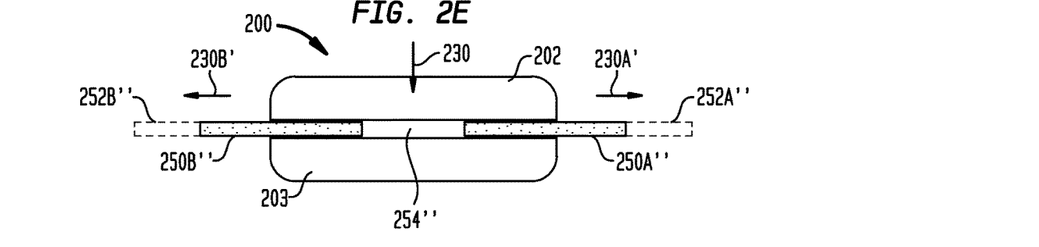
FIG. 2E is a cross section illustrating a later stage in the engagement of mating parts relative to the stage illustrated by FIG. 2A.
Figure 2F:
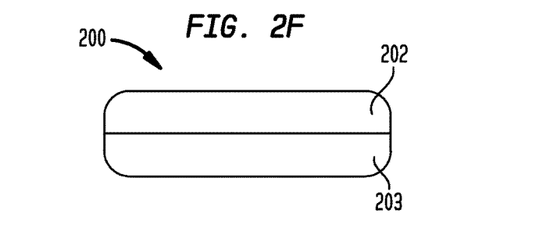
FIG. 2F is a cross section illustrating a later stage in the engagement of mating parts relative to the stage illustrated by FIG. 2A.

FIG. 2D is a top view of a wipe 250", according to another embodiment of the present technology. FIG. 2E is a cross section illustrating a later stage in the engagement of mating parts 202 and 203 relative to the stage illustrated by FIG. 2A, later in the process of clamping of wipe 250" by mating parts 202' and 203'. Wipe 250" is similar in many respects to wipes 250' and 250" of FIGS. 2A-2C, as indicated by similar numbering.

In FIG. 2D, forces substantially parallel to withdrawing directions 230A" and 230B" have been applied to tabs 252A" and 250B", causing wipe 250" to be cleaved (as indicated by splits 264A" and 264B") and portions of wipe 250" to be moved in directions 230A" and 230B", respectively, thereby cleaning surfaces 240 and 242. The removal of wipe 250" leaves a gap 254" between interfacing surfaces 240 and 242, with a length of gap 254" increasing as wipe 250" becomes progressively further withdrawn from mating parts 202 and 203, and with the height of gap 254" decreasing as mating parts 202 and 203 become progressively further engaged. FIG. 2F, again, is a cross section showing connector 200 after mating parts 202 and 203 are fully engaged.

In FIG. 2D, optional sets 262A" and 262B" of tear perforations are located along radii extending from hole 260" along directions substantially perpendicular the direction of tabs 250A" and 250B". In FIG. 2E, as a consequence of a portion of wipe 250 being dragged past the screw (not illustrated), wipe 250' has begun to be cleaved, as indicated by split 264'.

Figure 3A:
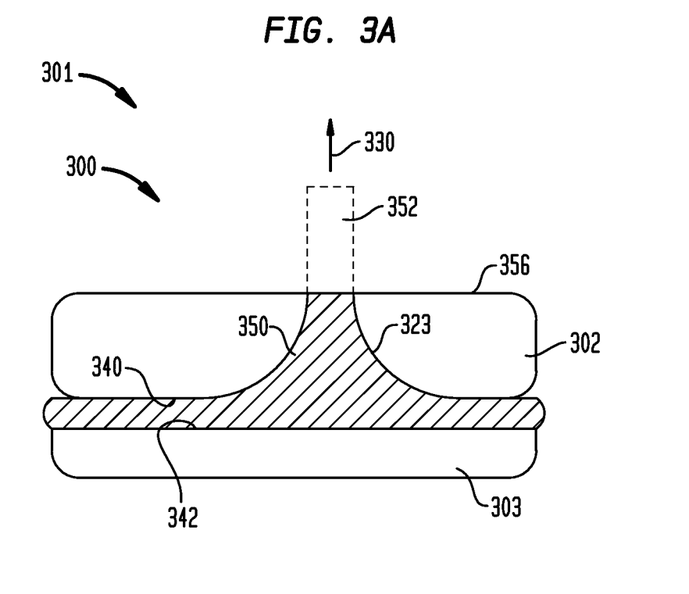
FIGS. 3A-3B are cross sections of another system, in which some embodiments of the present technology may be implemented, for cleaning mating parts of an implantable connector.
Figure 3B:
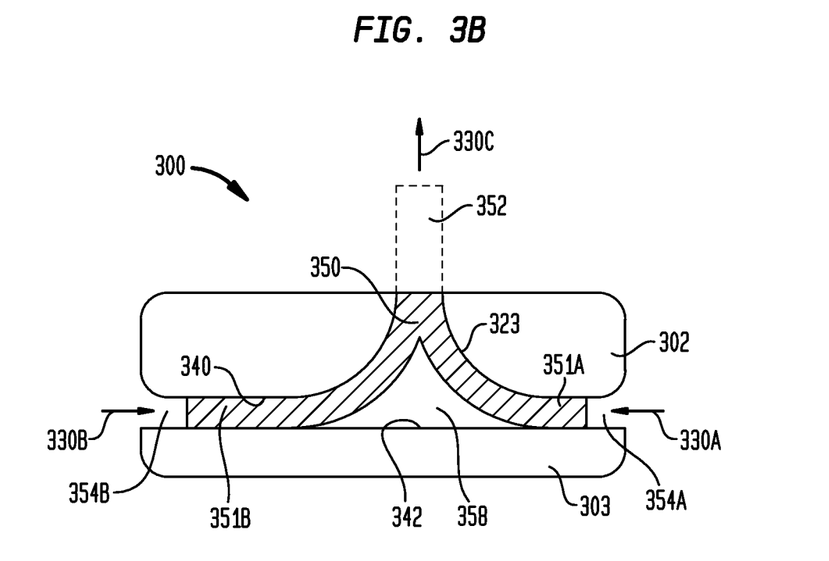

FIGS. 3A-3B are cross sections of a system 301, in which some embodiments of the present technology may be implemented, for cleaning mating parts of an implantable connector 300 using a wipe 350. Connector 300 is similar in many respects to connectors 100 and 200 of FIGS. 1A-1C and 2A-2F, as indicated by similar numbering, and in some respects has been illustrated in less detail for the sake of brevity. Wipe 350 is similar in many respects to wipe 250 of FIGS. 2A-2F, as indicated by similar numbering, and in some respects has been illustrated in less detail for the sake of brevity.

Assuming the replacement scenario, and to protect against risk of contamination, system 301 further includes: a cleaning structure 350, e.g., a dry wipe or wet wipe, configured to clean interfacing surfaces 240 and 242 as mating parts 202 and 203 are being engaged. Wipe 350 can be removably attached to interfacing surface 340 of mating part 302 so as to seal interfacing surface 340 from the ambient environment. In FIG. 3A, system 301 has been illustrated at the stage that interfacing surfaces 340 and 342 of mating parts 302 and 303 have begun to clamp wipe 350. Wipe 350 is configured to be withdrawn through through-hole 323, thereby cleaning interfacing surfaces 340 and 342. Wipe 350 can include an optional tab 352 that extends beyond an outer surface 356 of mating part 302. Tab 352 is configured to be grasped and thereby used to transfer a withdrawal force to cleaning structure 350 by which to withdraw wipe 350 from between interfacing surfaces 340 and 342.

FIG. 3B is a cross section illustrating a later stage in the engagement of mating parts 202 and 203 relative to the stage illustrated by FIG. 3A, later in the process of clamping of wipe 350 by mating parts 302 and 303.

In FIG. 3B, a force substantially parallel to a withdrawing direction 330C has been applied to tab 352, causing portions 351A and 351 B of wipe 350 to be moved in converging directions 330A and 330B, respectively. The removal of wipe 350 leaves gaps 354A and 354B between interfacing surfaces 340 and 342, with lengths of gaps 354A and 354B increasing as wipe 350 becomes progressively further withdrawn from mating parts 302 and 303, and with the height of gaps 354A and 354B decreasing as mating parts 302 and 303 become progressively further engaged. The removal of wipe 350 also leaves a gap 358 between interfacing surface 342 and wipe 350.

Figure 4A:
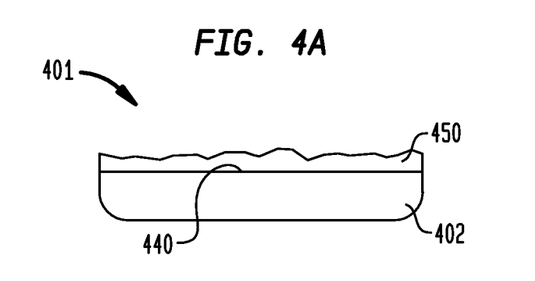
FIGS. 4A-4C together illustrate another system, in which some embodiments of the present technology may be implemented, for cleaning mating parts of an implantable connector.
Figure 4B:
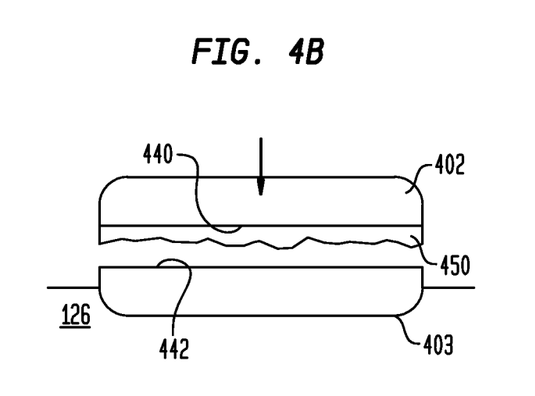
Figure 4C:
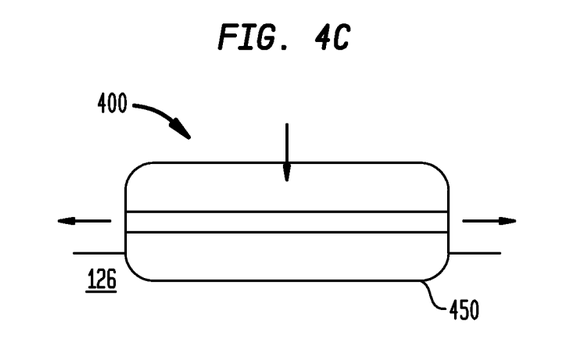

FIGS. 4A-4C together illustrate another system 401, in which some embodiments of the present technology may be implemented, for cleaning mating parts of an implantable connector 400. Connector 400 is similar in many respects to connectors 100 of FIGS. 1A-1C, as indicated by similar numbering, and in some respects has been illustrated in less detail for the sake of brevity.

Assuming the replacement scenario, and to protect against risk of contamination, system 401 further includes: a cleaning structure 450, e.g., a layer of foam material or viscous (e.g., gel) material, configured to clean interfacing surfaces 440 and 442 as mating parts 402 and 403 are being engaged. Layer 450 can be removably attached to interfacing surface 440 of mating part 402 so as to seal interfacing surface 440 from the ambient environment. In FIGS. 4A-4B, mating parts 402 and 403 are illustrated in a decoupled state.

In FIG. 4C, system 401 has been illustrated at the stage that interfacing surfaces 440 and 442 of mating parts 402 and 403 have begun to clamp wipe layer 450 thereby exerting a compression force on layer 450. The compression force is sufficiently large to extrude enough (if not substantially all) of layer 450 so that good electrical connections can be made between corresponding electrode pairs (not illustrated) provided on interfacing surfaces 440 and 442.

Figure 5A:
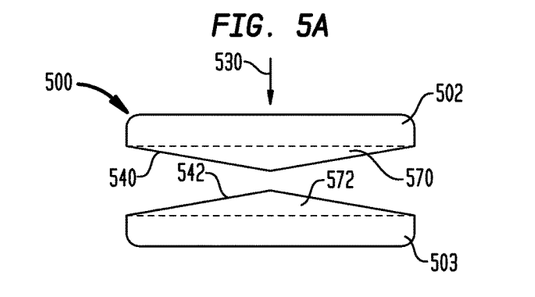
FIG. 5A is an exploded cross section of an implantable connector in a decoupled state, in which some embodiments of the present technology may be implemented.
Figure 5B:
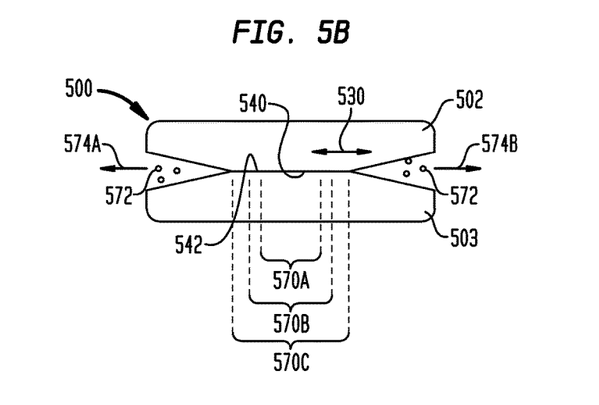
FIG. 5B is a cross section of the connector of FIG. 5A in an at least partially engaged state.

FIG. 5A is an exploded cross section of an implantable connector 500 in a decoupled state, in which some embodiments of the present technology may be implemented. FIG. 5B is a cross section of connector 500 in an at least partially engaged state. Connector 500 is similar in many respects to connector 100 of FIGS. 1A-C, as indicated by similar numbering, and in some respects has been illustrated in less detail for the sake of brevity.

Connector 500, e.g., a button type of connector, includes: a first detachable mating part 503 and a corresponding second detachable mating part 502, each of mating parts 502 and 503 being configured to be implantable in living tissue and terminate first and second segments (not illustrated) of a cable, respectively. In FIG. 5A, mating parts 502 and 503 are illustrated in a decoupled state. Mating parts 502 and 503 have interfacing surfaces 540 and 542. Corresponding electrode pairs (not illustrated) are provided on interfacing surfaces 540 and 542. FIGS. 5A-5B assume that mating part 503 is partially recessed in bone. The various components of connector 500 are formed of biocompatible materials, e.g., including one or more of Titanium, Silicone, Ceramic, Platinum, Platinum/Iridium, polyether ether ketone (PEEK), etc.

Connector 500 also includes, for example, a frictional engaging member (not illustrated), e.g., a screw, that can be inserted through a corresponding through-hole (not illustrated), e.g., an unthreaded through-hole, in mating part 502 and into a corresponding complementarily-shaped frictional engagement recess (not illustrated), e.g., a threaded hole, in mating part 503. When inserted through the through-hole into the hole, the screw applies a force to mating part 202 that urges mating part 502 to abut mating part 503, i.e., urges mating part 502 to couple with mating part 503. In other words, the screw applies a compression force upon mating parts 502 and 503. More particularly, the force applied by the screw urges corresponding electrodes (not illustrated) in pairs thereof to abut and thus to connect electrically, respectively. The force applied by the screw also resists a tendency of mating parts 502 and 503 to decouple. In addition, the through-hole and hole formed in mating parts 502 and 503, respectively, are formed in alignment so that the insertion of screw causes mating parts 502 and 503 to align, thereby facilitating good electrical connections between corresponding electrodes.

More particularly, mating parts 502 and 503 include resilient cleaning structures 570 and 572, respectively. Interfacing surfaces 540 and 542 are convex, e.g., conical. Resilient cleaning structures 570 and 572 are configured to progressively deform as second mating parts 502 and 503 become progressively more engaged with each other. A degree of contact between interfacing portions 540 and 542 progressively increases along a line substantially parallel to a line 530 as mating parts 502 and 503 become progressively more engaged. Such an increase in the degree of contact between interfacing portions 540 and 542 is illustrated in FIG. 5B by brackets 570A, 570B and 570C. As the degree of contact between interfacing portions 540 and 542 progresses, material 572 between mating parts 502 and 503 is progressively expelled in directions 572A and 572 B from between mating parts 502 and 503, thereby cleaning interfacing surfaces 540 and 542.

Figure 5C:
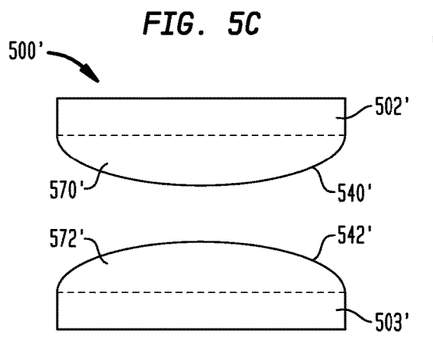
FIG. 5C is an exploded cross section of another implantable connector in a decoupled state, in which some embodiments of the present technology may be implemented.
Figure 5D:
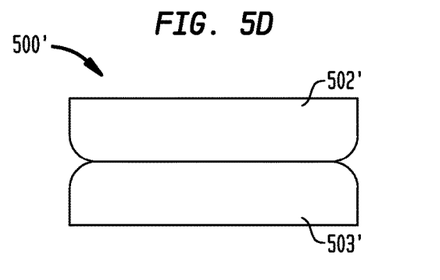
FIG. 5D is a cross section of the connector of FIG. 5A in an at least partially engaged state.

FIG. 5C is an exploded cross section of an implantable connector 500' in a decoupled state, in which some embodiments of the present technology may be implemented. FIG. 5D is a cross section of connector 500' in an at least partially engaged state. Connector 500' is similar in many respects to connector 500 of FIGS. 5A-5B, as indicated by similar numbering, and in some respects has been illustrated in less detail for the sake of brevity. More particularly, mating parts 502' and 503' include resilient cleaning structures 570' and 572', respectively. Interfacing surfaces 540' and 542' are convex, e.g., hemispherical.

Figure 6:
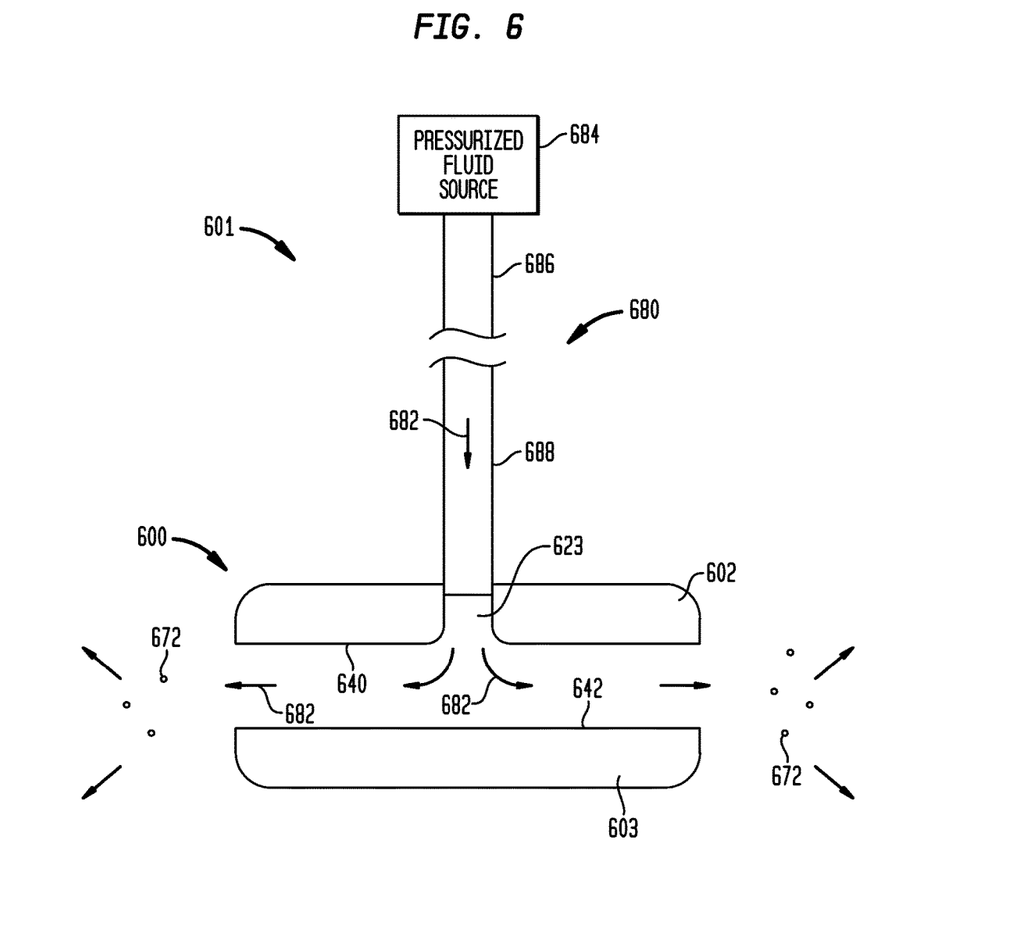
FIG. 6 is a cross section of another system, in which some embodiments of the present technology may be implemented, for cleaning mating parts of an implantable connector.

FIG. 6 is a cross section of a system 601, in which some embodiments of the present technology may be implemented, for cleaning mating parts of an implantable connector 600. Connector 600 is similar in many respects to connectors 100, 200, 300, 400, 500 and 500' of FIGS. 1A-1C, 2A-2F, 3A-3B, 4A-4C and 5A-5D, respectively, as indicated by similar numbering, and in some respects has been illustrated in less detail for the sake of brevity.

Connector 600 also includes, for example, a frictional engaging member (not illustrated), e.g., a screw, that can be inserted through a corresponding through-hole 623, e.g., an unthreaded through-hole, in mating part 602 and into a corresponding complementarily-shaped frictional engagement recess (not illustrated), e.g., a threaded hole, in mating part 603. In FIG. 6A, mating parts 602 and 603 are illustrated in a decoupled state.

Assuming the replacement scenario, and to protect against risk of contamination, system 601 further includes: a cleaning structure 680, e.g., a fluid-delivery arrangement, configured to provide pressurized fluid into through-hole 623 so as to deliver pressurized fluid 682 between first and second interfacing surfaces 640 and 642 and thereby clean the same by washing away contaminant material 672. For example, fluid 682 can be a gas, e.g., air, or a liquid, e.g., a bioresorbable liquid. Fluid-delivery arrangement 680 includes, e.g., a source 684 of pressurized fluid 682 and a hose 686 fitted with a nozzle 688 to deliver pressurized fluid 682. Nozzle 688 can be configured to fit into through-hole 623.

Figure 7:
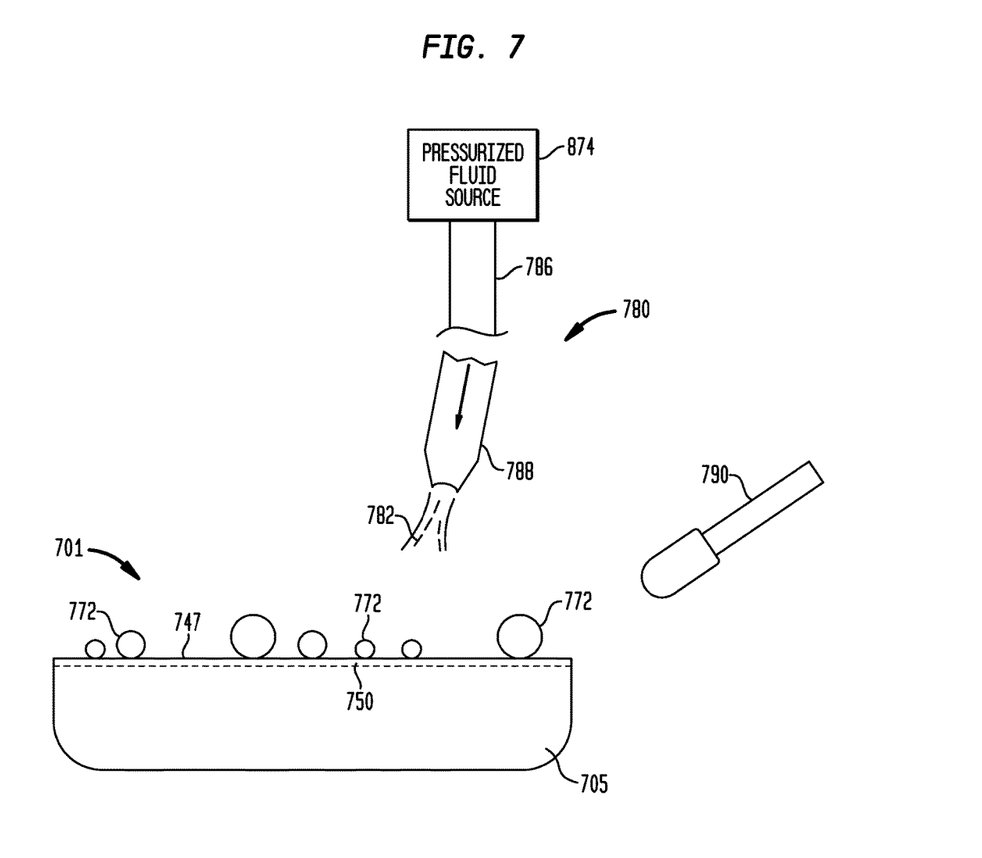
FIG. 7 is side view of another system, in which some embodiments of the present technology may be implemented, for cleaning a mating part of an implantable connector.

FIG. 7 is side view of another system 701, in which some embodiments of the present technology may be implemented, for cleaning a mating part 705 of an implantable connector. Mating part 705 can variously be similar in many respects to the mating parts 102-103 of FIGS. 1A-1C, 202-203 of FIGS. 2A-2F, 302-303 of FIGS. 3A-3B, 404-403 of FIGS. 4A-4C, 502-503 of FIGS. 5A-5B, 502'-503' of FIGS. 5C-5D, and 602-603 of FIG. 6, respectively, as indicated by similar numbering, and in some respects has been illustrated in less detail for the sake of brevity.

Mating part 705 is configured to be implantable in living tissue and terminate a segment (not illustrated) of a cable. Mating part 705 has an interfacing surface 747. Electrodes (not illustrated) are provided on interfacing surface 747 in correspondence to electrodes (not illustrated), respectively, on a corresponding mating part (not illustrated). Mating part 705 is formed of biocompatible materials, e.g., including one or more of Titanium, Silicone, Ceramic, Platinum, Platinum/Iridium, polyether ether ketone (PEEK), etc.

System 701 not only includes mating part 705, but also a protection structure 750 configured to facilitate removal of contamination material 772 from interfacing surface 747. For example, protection structure 750 includes a layer of hydrophobic and biocompatible material disposed on interfacing surface 747. The surface of layer 750 substantially corresponds to interfacing surface 747 but not necessarily entirely, e.g., the surface of layer 750 might not include the surfaces of the electrodes (again, not illustrated) formed in interfacing surface 747. Without being bound by theory, the contact angle (namely, the angle where a liquid/vapor interface meets a solid surface, as conventionally measured through the liquid) between the surface of layer 750 and the contamination material is sufficiently large so as to induce contamination 772 to bead. For example, the water contact angle of the surface of layer 747 is larger than 90°. Where layer 750 has a sufficiently low surface energy, e.g., if layer 747 includes a fluorinated material such as polytetrafluoroethylene (PTFE), it can exhibit a water contact angle of at least about 110°.

System 701 further includes: a removal device, e.g., a swab 790 and/or a fluid-delivery arrangement 780 configured to provide pressurized fluid 682 onto the surface of layer 750. For example, fluid 782 can be a gas, e.g., air, or a liquid, e.g., a bioresorbable liquid. Fluid-delivery arrangement 780 includes, e.g., a source 784 of pressurized fluid 782 and a hose 786 fitted with a nozzle 788 to deliver pressurized fluid 782.

Figure 8A:
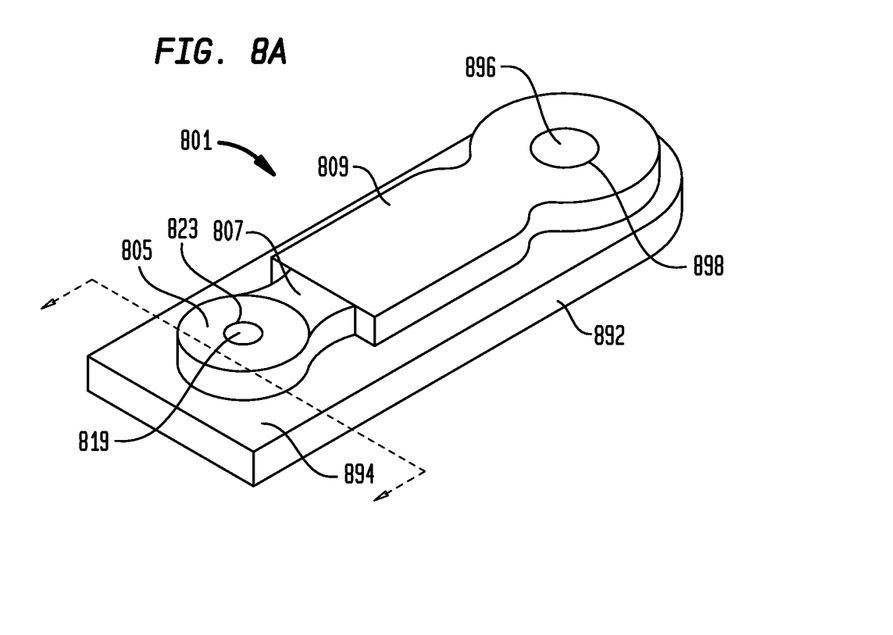
Figure 8B:
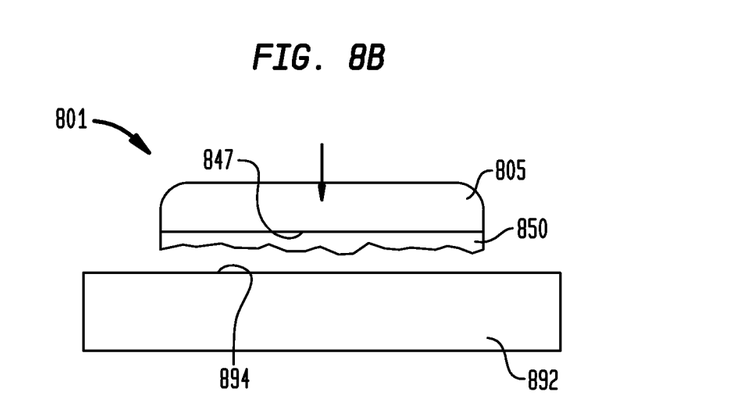
FIG. 8B is a cross-section, that together illustrate another system, in which some embodiments of the present technology may be implemented, for transporting a mating part of an implantable connector.

FIG. 8A is a three-quarter perspective view, and FIG. 8B is a cross-section, that together illustrate another system 801, in which some embodiments of the present technology may be implemented, for transporting a mating part 805 of an implantable connector. Mating part 805 can variously be similar in many respects to the mating parts 102-103 of FIGS. 1A-1C, 202-203 of FIGS. 2A-2F, 302-303 of FIGS. 3A-3B, 404-403 of FIGS. 4A-4C, 502-503 of FIGS. 5A-5B, 502'-503' of FIGS. 5C-5D, 602-603 of FIG. 6 and 705 of FIG. 7, respectively, as indicated by similar numbering, and in some respects has been illustrated in less detail for the sake of brevity.

Mating part 805 is configured to be implantable in living tissue and terminate a segment 807 of a cable. Mating part 805 has an interfacing surface 847. Electrodes (not illustrated) are provided on interfacing surface 847 in correspondence to electrodes (not illustrated), respectively, on a corresponding mating part (not illustrated). Mating part 805 is formed of biocompatible materials, e.g., including one or more of Titanium, Silicone, Ceramic, Platinum, Platinum/Iridium, polyether ether ketone (PEEK), etc.

System 801 not only includes mating part 805, but also a transportation structure 892, e.g., a backboard, configured for mounting mating part 805 thereon.

The implantable connector also includes, for example, a frictional engaging member, e.g., a screw 819, that can be inserted through a corresponding through-hole 823. e.g., an unthreaded through-hole, in mating part 805 and into a corresponding complementarily-shaped frictional engagement recess (not illustrated), e.g., a threaded hole, in the mating part corresponding to mating part 805. Backboard 892 is further configured with a frictional engagement recess (not illustrated) complementarily-shaped with respect to screw 819, e.g., a threaded hole. Accordingly, mating part 805 can be affixed to backboard 892 via screw 819 and the threaded hole in backboard 892.

Mating part 805 is connected to segment 807 of a cable at one end thereof. Segment 807 is attached at the other end to an implantable component 809. Together, mating part 805, segment 807 and component 809 comprise an implantable device. Among other things, backboard 892 impart structural rigidity to the implantable device, i.e., imparts structural rigidity to the assembly including mating part 805, segment 807 and component 809. Component 809 is configured with a through-hole 898, e.g., an unthreaded through-hole, for which backboard 892 has a corresponding second frictional engagement recess (not illustrated), e.g., a threaded hole, such that component 809 can be affixed to backboard 892 via a frictional engaging member 896, e.g., a screw, complementarily-shaped to the second frictional engagement recess.

First mating part 805 is further configured to have an interfacing surface 847, and backboard 892 is further configured to have a mounting surface 894. System 801 is arranged to mount interface surface 847 against mounting surface 894 so as to protect interface surface 847. Optionally, system 801 can further include a layer 850 of cleaning material disposed between interfacing surface 847 and mounting surface 894.

For ease of description, the present disclosure has discussed implantable conductor embodiments in example implementations as button-type connectors. Other implementations, however, are contemplated, e.g., as header-type connectors. Alternatively, for example, implantable connector 100 could be implemented as a header type of connector, e.g., as a linear pacemaker connector. In a header-type connector implementation of connector 100, e.g., second segment 114 of the cable would not be present. Rather, detachable mating part 103 would be incorporated into a header/housing.

The present technology described and claimed herein is not to be limited in scope by the specific example embodiments herein disclosed, since these embodiments are intended as illustrations, and not limitations, of several aspects of the present technology. Any equivalent embodiments are intended to be within the scope of the present technology. Indeed, various modifications of the present technology in addition to those shown and described herein will become apparent to those skilled in the art from the foregoing description. Such modifications are also intended to fall within the scope of the appended claims.

What is claimed is:

1. A system, comprising:
an implantable connector including first and second detachable mating parts configured:
to be implantable in living tissue;
to terminate at least a first segment of a cable; and
to have first and second interfacing surfaces, respectively; and
a cleaning structure configured to clean the first and second interfacing surfaces as the first and second mating parts are being engaged.

2. The system of claim 1, wherein:
the cleaning structure is further configured to be compressed between the first and second interfacing surfaces of the engaging first and second mating parts.

3. The system of claim 2, wherein:
the cleaning structure is further configured to be withdrawn from between the first and second interfacing surfaces while being compressed by the same.

4. The system of claim 3, wherein:
the second mating part is further configured with a through-hole;
the connector further includes:
a frictional engaging member;
the first mating part is further configured with a frictional engaging recess corresponding to, and complementarily-shaped with respect to, the frictional engaging member; and
the member is insertable into the recess;
cleaning structure is further configured with a hole through which passes the member when the member extends from the second mating part into the first mating part.

5. The system of claim 4, wherein:
the member is a screw; and
the recess is a threaded hole.

6. The system of claim 4, wherein:
the cleaning structure is further configured to facilitate being cleaved, at least in part, by the member as the cleaning structure is being withdrawn from between the first and second interfacing surfaces.

7. The system of claim 6, wherein:
the cleaning structure includes one or more tabs that overhang one or more corresponding edges of the first and second mating parts;
each tab being configured to be grasped and thereby used to transfer a withdrawal force to the cleaning structure by which to withdraw at least a corresponding part thereof from between the first and second interfacing surfaces.

8. The system of claim 7, wherein:
the cleaning structure is further configured with one or more sets of tear perforations corresponding to the one or more tabs, each set of tear perforations being located substantially along a radius extending from the hole along at least one of the following directions:
a direction substantially opposite to the corresponding tab; and
a direction substantially perpendicular to the corresponding tab.

9. The system of claim 1, wherein:
the cleaning structure is further configured to facilitate being cleaved, at least in part, by a force applied to the cleaning structure for withdrawing the same from between the first and second interfacing surfaces.

10. The system of claim 9, wherein:
the cleaning structure is further configured with one or more sets of tear perforations to facilitate the at least cleaving of the cleaning structure.

11. The system of claim 1, wherein:
the cleaning structure is a dry wipe.

12. The system of claim 11, wherein:
the wipe includes a nonwoven fabric.

13. The system of claim 11, wherein:
the cleaning structure is a wet wipe the liquid of which includes at least one cleaning additive.

14. The system of claim 1, wherein:
the cleaning structure is a removable layer of material disposed in contact with one of the first and second interfacing surfaces so as to seal the same from the ambient environment.

15. The system of claim 1, wherein:
the second mating part is further configured with a centrally located through-hole; and
the cleaning structure is further configured to be withdrawn through the through-hole.

16. The system of claim 1, wherein:
the cleaning structure is a layer of foam or viscous material temporarily adhered to at least one of the first and second mating parts.

17. The system of claim 1, wherein:
the second mating part is further configured with a through-hole;
the cleaning structure includes:
a fluid-delivery arrangement configured to provide pressurized fluid into the through-hole so as to deliver the pressurized fluid between the first and second interfacing surfaces and thereby wash the same.

18. The system of claim 17, wherein:
the fluid is one of a gas and a bioresorbable liquid.

19. The system of claim 17 the wherein the fluid-delivery arrangement includes:
a source of the pressurized fluid; and
a nozzle configured to direct the pressurized fluid from the source into the through-hole.

20. The system of claim 1, wherein:
the cleaning structure is a removable layer of material disposed in contact with one of the first and second interfacing surfaces so as to seal the same from the ambient environment.

21. The system of claim 1, wherein:
the cleaning structure is further configured to be withdrawn from between the first and second interfacing surfaces while being located between the surfaces.

22. The system of claim 1, wherein:
the cleaning structure is further configured to be withdrawn in parts from the implantable connector, a first part of the parts being withdrawn in one direction, a second part of the parts being withdrawn in a direction at least substantially opposite of the first direction.

23. A system, comprising:
a first implantable mating part of a connector terminating a first segment of a first cable;

a second implantable mating part of a connector terminating a second segment of a cable, wherein the first and second detachable mating parts are configured:
  to be implantable in living tissue; and
  to have first and second interfacing surfaces, respectively; and
a cleaning structure configured to clean the first and second interfacing surfaces as the first and second mating parts are being engaged, the cleaning structure being interposed between the first and second interfacing surfaces and being removable when a compression force is applied to the cleaning structure via the first implantable mating part and the second implantable mating part such that upon removal of the cleaning structure when the compression force is applied, the first and second surfaces are cleaned.

24. A system for cleaning mating parts of an implantable connector comprising:
an implantable connector including first and second detachable mating parts configured:
  to be implantable in living tissue;
  to terminate at least a first segment of a cable; and
  to have first and second interfacing surfaces, respectively; and
a cleaning structure configured to clean the first and second interfacing surfaces as the first and second mating parts are being engaged.

25. The system of claim 24, wherein:
the first mating part includes a through hole extending from a first face of the first mating part to a second face of the mating part, the second face of the mating part including the first interfacing surface, the first face and the second face being opposite one another; and
the cleaning structure includes a component that extends from the location between the first and second mating parts, through the hole to a location above the first face.

26. The system of claim 24, wherein:
the cleaning structure is further configured to be compressed between the first and second interfacing surfaces of the engaging first and second mating parts.

27. The system of claim 24, wherein:
the cleaning structure is further configured to be withdrawn from between the first and second interfacing surfaces while being located between the surfaces.

28. The system of claim 27, wherein:
the second mating part is further configured with a through-hole;
the connector further includes:
  a frictional engaging member;
the first mating part is further configured with a frictional engaging recess corresponding to, and complementarily-shaped with respect to, the frictional engaging member; and
the member is insertable into the recess;
cleaning structure is further configured with a hole through which passes the member when the member extends from the second mating part into the first mating part.

29. The system of claim 28, wherein:
the member is a screw; and
the recess is a threaded hole.

* * * * *